United States Patent [19]

Leach et al.

[11] 4,235,970

[45] Nov. 25, 1980

[54] PROTEASE INACTIVATED α-AMYLASE PREPARATIONS

[75] Inventors: Harry W. Leach, Willowbrook; Ronald Hebeda, Naperville, both of Ill.

[73] Assignee: CPC International Inc., Englewood Cliffs, N.J.

[21] Appl. No.: 712,103

[22] Filed: Aug. 5, 1976

[51] Int. Cl.$^3$ ............................................. C12N 9/28
[52] U.S. Cl. .................................. 435/202; 435/813; 435/836
[58] Field of Search ....................... 195/63, 62, 64, 65, 195/66 R, 68, 121, 122, 125; 435/202

[56] References Cited

U.S. PATENT DOCUMENTS

| 2,683,682 | 7/1919 | Miller et al. | 195/66 R |
|---|---|---|---|
| 3,039,936 | 6/1962 | Lenney et al. | 195/11 |
| 3,249,512 | 5/1966 | Bode | 435/96 |
| 3,303,102 | 2/1967 | Armbruster | 195/31 R |
| 3,819,528 | 6/1974 | Berry | 195/63 X |
| 3,912,590 | 10/1975 | Slott et al. | 195/31 R |

FOREIGN PATENT DOCUMENTS

| 37-16696 | 10/1962 | Japan. | |
| 269889 | 8/1970 | U.S.S.R. | 195/65 |

*Primary Examiner*—Lionel M. Shapiro

[57] ABSTRACT

Protease enzyme impurities contained in bacterial α-amylase enzyme preparations are inactivated by a mild heat treatment in the presence of a protective material. Useful protective materials include calcium and starch hydrolysates such as corn syrup. The protease-free α-amylase can then be used to solubilize starch materials by various granular starch and conventional processes. Hydrolysates obtained contain significantly less soluble protein than those prepared using untreated α-amylases. A preferred α-amylase enzyme preparation is one derived from a *Bacillus licheniformis* microorganism.

4 Claims, No Drawings

PROTEASE INACTIVATED α-AMYLASE PREPARATIONS

This invention relates to the selective inactivation of one enzyme in the presence of another, and more in particular, it relates to the selective inactivation of the proteolytic enzyme activity which exists in conjunction with α-amylase activity in crude bacterial α-amylase enzyme preparations.

α-Amylase is an enzyme preparation which is used to digest or liquefy starch materials as the initial step in the production of a number of sweeteners, such as dextrose, levulose, maltose, and high D.E. corn syrups. The α-amylase hydrolyzes starch molecules to break them down into a variety of lower molecular weight fragments. These products are subsequently treated with one or more additional enzyme preparations including glucoamylase, β-amylase and glucose isomerase in order to produce the desired final product. Alternatively, a plurality of these enzyme preparations may be introduced into a slurry of the starch material simultaneously to directly produce the sweetener materials.

α-Amylase enzyme preparations are available from a wide variety of sources. It is economically and most commercially feasible to utilize α-amylases which are produced from bacterial sources. Certain bacterial organisms, such as *Bacillus subtilis, Bacillus licheniformis,* etc., are cultivated in large vats, the cells are then destroyed and the enzyme preparation separated from the broth and purified. However, this "purified" α-amylase enzyme preparation still retains certain impurities which are difficult and expensive to remove.

One such detrimental impurity is known as protease or proteolytic enzyme. This biologically active material can react with various proteinaceous materials present in the starchy materials to produce hydrolysates containing peptides, polypeptides and amino acids.

The presence of the protease enzyme contaminant in the α-amylase is detrimental in the hydrolysis of the starch containing material. In general, different types of starch materials will contain differing amounts of proteinaceous materials. For example, a refined corn starch material may contain as little as 0.3% protein, a dry milled product, such as corn grits may contain up to about 8 or 10% protein and unrefined starch materials called mill starches, may contain as much as 20% proteinaceous materials. When the starch material is hydrolyzed using the α-amylase enzyme preparation the presence of the protease activity in the preparation causes a fraction of the protein material to be hydrolyzed simultaneously with the starch. This results in the loss of economically valuable protein products. In addition, these undesirable by-products must be removed from the final sweetener product at extra cost.

It is economically desirable to utilize the least expensive starting material possible to produce the starch hydrolysates. Thus, a mill starch, which has only undergone the removal of fiber and germ is preferable to a refined starch which has a low protein content. When utilizing an α-amylase enzyme preparation which includes substantial amounts of protease activity, it is necessary to use relatively expensive refined starch materials because of their low protein levels. The use of such enzyme preparations on less refined starch materials would produce excesses of protein hydrolysate materials which would interfere with the subsequent uses and conversions of the starch hydrolysate.

If the α-amylase enzyme preparation is substantially free of proteolytic enzyme activity, the proteins contained in the starch material being hydrolyzed will not be hydrolyzed to any appreciable degree but will remain with the insoluble matter and may be filtered and recovered in an efficient manner.

It is not essential that all of the proteolytic enzyme activity be removed or inactivated in the α-amylase enzyme preparation. While it is preferable that this proteolytic activity be reduced to as low a level as possible, it has been found that if the ratio of proteolytic enzyme activity, U/g, to amylolytic enzyme activity, U/g, (the P/α ratio) is less than about 2, the enzyme preparation will function in a satisfactory manner for the purposes of this invention. It is most preferred that this ratio be less than about 0.8. As used herein, the term protease-free α-amylase will mean an α-amylase enzyme preparation where this ratio is less than about 2.

The protease-free α-amylases of this invention are useful in producing starch hydrolysates from a variety of starchy materials. These may be derived from any, source such as corn, wheat, rice, potato, and grain sorghum. Waxy varieties may be used. In the United States, starchy materials derived from corn are generally preferred for economic reasons, whereas starchy materials derived from wheat and rice are preferred in other parts of the world.

The starchy material may be any of a variety of partially purified products; i.e., dry materials, one example of which is corn grits (others include corn cleanings, corn flour, wheat flour, etc.), or wet products such as mill starch and more refined products from which a portion of the gluten has been removed. As used herein, the term "mill starch" is used to mean any of several partially purified starch slurries ranging from a very crude product from which only the fiber and germ have been removed to a purified material containing less than about 0.3% proteinaceous materials. "Light" mill starch refers to the starch slurry as received from the fiber and germ separators while "heavy" mill starch refers to a similar material from which a portion of the water has been removed. Pure starches may also be used.

The protease-free α-amylases of this invention are useful to form starch hydrolysates by the usual methods. They are particularly adapted to use in procedures wherein the residual unconverted starch remains in its granular form. These processes are generally described and claimed in U.S. Pat. Nos. 3,922,196; 3,922,197; 3,922,198; 3,922,199; 3,922,200 and 3,922,201, all issued November 25, 1975, the contents of which are incorporated herein by reference.

In the granular starch procedures, at least the initial solubilization of the starchy material is carried out at relatively low temperature, i.e., below the actual gelatinization temperature of the particular starch contained in the starch material. At these temperatures, the protease activity represents a particular problem as it is not inactivated to any substantial extent. When using conventional procedures which utilize higher temperatures, the proteolytic enzymes will be inactivated to a partial extent during use.

A number of procedures have been suggested in the prior art for removing, reducing or inactivating the proteolytic or other enzyme impurities in α-amylase and other enzyme preparations.

For example, U.S. Pat. No. 3,249,512 suggests the inactivation of liquefying enzymes in an amyloglucosidase preparation by heating to about 210° F.; U.S. Pat.

No. 2,683,682 discloses the differential inactivation of α-amylase and proteinase mixtures by adjusting the pH of the mixture and heating to selectively inactivate one of the enzymes; U.S. Pat. No. 3,912,590 suggests that the protease in an α-amylase derived from *Bacillus licheniformis* may be inactivated during a starch liquefaction by carrying out at least the initial portion of the process at a temperature of 100° C. to 115° C.; U.S. Pat. No. 3,303,102 suggests the use of a starch hydrolysate to buffer a fungal amylase preparation from inactivation during the acid inactivation of transglucosidase. Further, Japanese Patent Specification No. 16696/62 discloses that proteolytic enzyme solutions may be established by a combination of polyhydric alcohols and calcium salts.

It has been found that the crude bacterial α-amylase enzyme preparation may have the protease activity reduced by heating the crude preparation to a predetermined temperature for a predetermined period of time in order to inactivate the protease. Prior to this heat treatment, the crude bacterial α-amylase enzyme preparation is admixed with a material which is capable of protecting the α-amylase from heat inactivation. A preferred protective material is a carbohydrate substrate material such as corn syrup. Alternatively, as another preferred embodiment, α-amylase preparations derived from *Bacillus licheniformis*, which are particularly heat stable, may have the proteolytic activity reduced by a similar heat treatment but utilizing calcium ion as the protective material.

By inactivation of the enzyme preparations, it is meant the reduction of the defined activity of the protease enzyme to less than the above-defined ratio. The α-amylase activity of the enzyme preparation is determined in accordance with the procedure outlined in U.S. Pat. No. 3,922,199, issued Nov. 25, 1975.

A unit of protease enzyme activity is defined in the quantity of enzyme that produces trichloroacetic acid soluble fragments giving a blue color equivalent to 0.5 $\mu g$ of tyrosine under the following assay procedure.

A standard casein solution is prepared by dissolving 2.00 g. of casein in 20.0 ml of 1.0 N NaOH. 50 ml of water is added and the pH adjusted to 6.3 with dilute phosphoric acid (1 part 85% acid to 3 parts water, V/V). Water is added to make 100 ml.

A tyrosine stock solution is prepared by dissolving 250.0 mg of 1-tyrosine in 0.2 N HCl to make 500 ml solution. This solution contains 500 $\mu g$ tyrosine per ml.

A Folin Phenol Reagent solution is prepared by diluting 100 ml of Phenol reagent (2 N Folin and Ciocalteau, Fisher Scientific Co.) with 300 ml of water.

A standard curve is prepared as follows.

Pipet 1.0, 2.0, 3.0, 4.0, 5.0 and 6.0 ml of the stock tyrosine solution into each of six 50 ml volumetric flasks and dilute to mark with 0.2 N HCl. The resulting solutions contain 10, 20, 30, 40, 50 and 60 $\mu g$ tyrosine/ml. Pipet 3.0 ml of each solution into a 25×150 mm test tube. Prepare a blank containing 3.0 ml of 0.2 N HCl. Pipet 15.0 ml of 0.4 M $Na_2CO_3$ and 3.0 ml of Folin phenol reagent into each test tube and mix with a Vortex mixer. Place in a 37° C. water bath for 20 minutes to develop color. Determine absorbance of each sample relative to distilled water in a 1 cm cuvette at 660 nm. Subtract blank absorbance from each sample absorbance and plot corrected absorbance vs. $\mu g$ tyrosine per ml. Absorbance values should be in the range of 0.10 to 0.60.

The protease assay procedure is as follows.

Prepare a solution of enzyme containing 20–100 protease U/ml by adding a known weight of enzyme preparation to a 500 ml volumetric flask and diluting to the mark with 0.1% W/V calcium acetate solution. Pipet 1.0 ml of enzyme solution into each of two 15 ml centrifuge tubes in a 37° C. constant temperature water bath (one tube is used for the sample, the other for a blank). Allow to equilibrate for 5 minutes. Using blow-out pipets add 1.0 ml of casein solution to the sample and 2.0 ml of 0.4 M trichloroacetic acid to the blank and mix using a Vortex mixer. After exactly 10 minutes reaction time, pipet 2.0 ml of 0.4 M trichloroacetic acid into the sample and 1.0 ml casein solution into the blank.

Mix each sample as before and continue incubation at 37° C. for an additional 20 minutes. Remove samples from bath and immediately centrifuge at 2000 rpm for 10 minutes. Decant each supernate into a 25×150 mm test tube and mix thoroughly. Pipet 2.0 ml of each supernate into a 25×150 mm test tube. Pipet 10.0 ml of 0.4 M $Na_2CO_3$ and 2.0 ml Folin phenol reagent into each test tube and mix. Place test tubes in a 37° C. water bath and incubate for exactly 20 minutes to develop color. Determine absorbance relative to distilled water in a 1 cuvette at 660 nm. Subtract blank absorbance from sample absorbance to obtain net absorbance, and determine apparent tyrosine concentration from the standard curve. The protease activity is then Protease Activity, U/g = apparent tyrosine $\mu g/ml \times 2 \times 2$ dilution factor.

In accordance with the first embodiment of this invention, any bacterial α-amylase may be utilized. These preparations are derived from a variety of materials. These are standard commercial materials that are sold under a variety of tradenames. Particularly preferred in the practice of this invention are α-amylase enzyme preparations which have a relatively high heat stability, such as those preparations sold under the trademark THERMAMYL, manufactured by Novo Terapeutisk Laboratorium, Copenhagen, Denmark. These enzyme preparations are derived from certain strains of *Bacillus licheniformis* as generally described in British Pat. No. 1,296,839 which have a relatively high heat stability. Other useful enzyme preparations are those which are derived from *Bacillus subtilis*, such as those sold under the trademarks RAPIDASE and TENASE.

The bacterial α-amylase enzyme preparation is first admixed with a protective material. Suitable protective materials in general are carbohydrate based materials which are capable of reducing the heat degradation of the α-amylase enzyme activity in the preparation. These same protective materials do not in general afford protection for the proteolytic enzyme activity to the same extent as the α-amylase. Generally, the protective materials which are preferred in the preferred in the practice of this invention are materials which are capable of being attacked by the α-amylase and thus capable of protecting the active site; for example, starch hydrolysate materials having a D.E. in the range of up to about 50; for example, a 9–11 D.E. hydrolyzed cereal solid product (e.g., a maltodextrin) sold under the trademark of MOR-REX by CPC International Inc., Englewood Cliffs, N.J., or a corn syrup of 42 D.E., also sold by CPC International Inc. Dextrose may also be used as the protective material with some reduction in efficiency. Similarly, if the starch hydrolysate has a D.E. of substantially above 50, the amount of protective action will be reduced. These protective materials, when present on a volume basis in the range of about 2:1 to about 1:2, protective material to enzyme, substantially reduce the rate of heat inactivation of the α-amylase activity. The volume basis is predicated on using a 30% d.s. protective material with the enzyme preparation. As commercial enzyme preparations are generally about 30% d.s., the volume ratios are substantially the same as the weight (dry substance) ratios. Generally, a preferred amount of the hydrolysate materials will be about 70%, dry basis.

The hydrolysate material is admixed into the crude bacterial α-amylase enzyme preparation and then the mixture is heated to a temperature in the range of from about 70° C. to about 90° C. for a period of time which is sufficient to inactivate the proteolytic enzyme activity without substantially reducing the α-amylase enzyme activity. Generally, a temperature of about 80° C. is preferred. The time during which the temperature is maintained will depend on the degree of proteolytic enzyme activity reduction needed and the particular temperature utilized. Generally, periods of 15 minutes to 60 minutes are sufficient, although periods of up to three hours may be used. In general, enzyme preparations derived from *Bacillus subtilis* require shorter heating times than those derived from *Bacillus licheniformis*. For example, at 80° C., from about 15-30 minutes is a sufficient period of time for preparations derived from *Bacillus subtilis*, while those derived from *Bacillus licheniformis* require from about 45 to 60 minutes.

The use of the starch hydrolysate materials as protective materials have the further advantage that essentially no impurities are introduced which need to be removed in later steps. The α-amylase enzyme preparation is to be used to produce starch hydrolysate materials and the introduction of substantial quantities of previously formed hydrolysate materials will not cause later purification problems. In contradistinction, when following the second embodiment of this invention, whereby the protective material comprises calcium ion, the calcium ion is an impurity which must later be removed from the final product.

The second preferred embodiment of this invention utilizes calcium ion as the protective material. This embodiment is particularly useful when using relatively heat stable α-amylases such as those derived from *Bacillus licheniformis*.

When utilizing this procedure, the total calcium ion present in the system must be considered, including that already present in the crude preparation. As the calcium ion content varies from batch to batch, it is necessary to determine the calcium ion present. A water soluble calcium salt may then be added to bring the calcium ion concentration up to a predetermined level.

It is important to note that the presence of calcium ion tends to protect the protease activity as well as the α-amylase activity. Hence, at higher calcium levels a relatively longer heat treatment period may be necessary to essentially completely inactivate the protease enzyme.

The concentration of the calcium ion which will provide sufficient protection to the α-amylase activity has been found to be in the range of about 0.5% to about 1.5%, dry basis, of enzyme. Preferably, the concentration is at least about 1.0%, dry basis. Concentrations of 2.0% calcium ion or more appear to have a detrimental effect.

Generally, the protease level in a *Bacillus licheniformis* α-amylase, such as THERMAMYL, is reduced by about 90% by merely heat treating the "as is" (about 1.0% $CA^{++}$) enzyme for 60 minutes at 80° C. Only 5% loss in α-amylase activity is observed.

The protease free α-amylase preparations may then be used to produce starch hydrolysates from a variety of high protein starch sources such as corn, milo, wheat, etc. These include both dry and wet-milled products, such as corn grits, various grades of mill starch, wheat clears, etc. The use of the α-amylases which have had the protease activity inactivated in accordance with this invention for the hydrolysis of the various starch sources produced hydrolysates equivalent in carbohydrate composition to those produced from prime starch. It is also possible to utilize α-amylase enzyme preparations which are already free of any substantial amount of proteolytic activity, such as the preparation sold under the trademark MAXAMYL LX 6000, sold by Gist-Brocades, Delft, The Netherlands (derived from *Bacillus subtilis*).

Satisfactory results have been obtained using both the hydrolysis procedures avoiding gelatinization of the starch as described in the aforementioned patents and conventional enzyme-enzyme hydrolysis procedures.

The following enzyme preparations were utilized producing hydrolysates from the starch sources.

1. THERMAMYL 60 α-amylase, Batch AN-1009 from *Bacillus licheniformis*. The original protease activity was 33,084 U/g and α-amylase activity 1006 U/g. One volume of enzyme was diluted with two volumes of 30% d.s. 42 D.E. corn syrup. The mixture was heated from room temperature to 80° C. in 30 minutes, held at 80° C. for 75 minutes and then cooled in an ice bath. This resulted in an α-amylase activity of 323 U/g and a protease activity of 520 U/g.

2. MAXAMYL LX-6000 α-amylase from a *Bacillus subtilis* having an α-amylase activity of 14,955 U/g. This enzyme had a protease/α-amylase ratio of less than 1 and was used "as is".

3. Glucoamylase derived from *Aspergillus niger* having an activity of 284 glucoamylase U/g.

The following sources of starch were utilized with satisfactory results.
1. Corn Grits: a dry milled corn product.
2. Corn Cleanings: fines from the screenings of corn kernels.
3. Wheat Clears: a dry milled wheat product.
4. Light Mill Starch: a degermed starch slurry containing 10-12% protein.
5. Heavy Mill Starch: a concentrated slurry.
6. Second Hydroclone Underflow: a mill starch slurry where the protein has been reduced to about 1-1.5%.

It is necessary to prewash the starch materials prior to introducing the α-amylase enzyme preparation to remove soluble materials, primarily ash and protein.

It is preferable that the prewash be carried out at about room temperature as at higher temperatures there may be increased solubilization of proteinaceous and carbohydrate materials.

When using dry milled products such as corn grits or corn cleanings, the prewashing is carried out by slurrying one part of the starch material in 2 parts by weight of water containing from about 200 ppm to about 1000 ppm, and preferably about 500 ppm $SO_2$ for about ½ hour at room temperature. The slurry is filtered and washed with at least one additional part of the $SO_2$ solution.

When using wet milled materials which are in slurry form which already includes $SO_2$, one needs to merely filter and wash with water. Alternatively, these materials may also be washed with the SO₂ solution.

The granular starch enzyme conversion method (GS-EHE) is performed in accordance with the following procedure:

The resulting cake is slurried into water to 30% solids and converted as follows:

Attemperate slurry at 60° C., add 50 ppm Ca++ on a starch dry basis, adjust pH and add 1 U P.I. (protease inactivated) THERMAMYL/g d.s. Heat to 75° C. at 1° C./5 minutes up to 70° C., then at 1° C./15 minutes to 75° C. Place in boiling water bath, allow 15 minutes at 75° C., heat treat at 100° C. and hold 15 minutes. Cool to 60° C., adjust the pH to 4.3, add 0.14 U glucoamylase/g d.s. or adjust the pH to 5.5 and add 0.2% malt extract. Adjust all final hydrolyzates to pH 4.3 prior to filtration. The initial pH adjustment should be to about 6.5 when using wet milled high protein materials, and about 5.5 when using dry milled materials or starches which have been purified of proteins.

As the gelatinization temperature range for wheat starch is approximately 10° C. lower than for corn starch, the thinning temperature profile is changed to a 50° C. to 65° C. cycle.

The barley malt extract was prepared by stirring 10.38 grams of ground malt in 79.26 grams H₂O for 1 hour then filtering by gravity through Whatman #1 paper. Thus, 10 ml of the filtrate is equivalent to 1.2 g d.b. malt.

In similar fashion, the other above-mentioned granular starch or conventional procedures may be used.

The protease-free α-amylase preparations may also be utilized in granular starch or conventional procedures using a prime starch as the starting material.

derived from *Bacillus licheniformis*. The preparation is mixed with the substrate material and then held at 80° C. for the designated period of time. It can be seen by an examination of this data that the 11 D.E. corn syrup and the 42 D.E. corn syrup protect the α-amylase activity against heat inactivation whereby products are generated which have a P/α activity ratio in the desired range. However, the dextrose does not protect the α-amylase activity as well.

It is important to note with respect to Example I and also for the following Examples, that the protease assay is performed at a pH range from about 6.2 to about 6.4, even though the pH during use is possibly lower, such as a pH of about 5.5. However, this has been found to be necessary as protease assays at a pH of 5.5 are not linear with sample size.

Table I shows the results of Example I. Heat treatment in the presence of the 11 D.E. or 42 D.E. substrate results in about 93% and 96% protease inactivation, respectively, at enzyme to substrate ratios of 1 to 1 and 1 to 2, respectively. No significant loss in α-amylase activity is observed in either ratio. However, when dextrose is used as the protective substrate material, only 89% to 92% protease inactivation is obtained with about 12% reduction in α-amylase activity.

It has also been determined that in the presence of corn syrup, increasing heat treatment time from 60 to 75 or to 90 minutes increases protease inactivation only slightly; i.e., from about 91% to 95%, without significant loss of α-amylase activity. Reducing heat treatment time, however, results in a significant decrease in protease inactivation to only 73% after 30 minutes. It is important to note that essentially the same degree of protease inactivation also was obtained using corn syrup which was adjusted to a pH level of 5.5 or 7.0.

TABLE I

EFFECT OF SUBSTRATE TYPE AND CONCENTRATION ON INACTIVATION OF PROTEASE DURING HEAT TREATMENT OF THERMAMYL[a] AT 80° C.

| Substrate | Vol. Ratio Enzyme: Substrate | Heat Treatment Time, min | pH | Protease Act.,[c] U/ml Untreated | Heat Treated | % Prot. Inact. | α-Amylase Act., U/ml Untreated | Heat Treated | % α Inact. | P/α Act. Ratio |
|---|---|---|---|---|---|---|---|---|---|---|
| 11 D.E. Corn Syrup | 1:1 | 60 | 6.4 | 17,080 | 1,325 | 92.2 | 591 | 585 | Nil | 2.3 |
| 11 D.E. Corn Syrup | 1:2 | 60 | 6.4 | 11,387 | 485 | 95.7 | 394 | 391 | Nil | 1.2 |
| 42 D.E. Corn Syrup | 1:1 | 60 | 6.4 | 17,080 | 1,190 | 93.0 | 591 | 603 | Nil | 2.0 |
| 42 D.E. Corn Syrup | 1:2 | 60 | 6.4 | 11,387 | 465 | 95.9 | 394 | 396 | Nil | 1.2 |
| Dextrose | 1:1 | 60 | 6.3 | 17,080 | 1,850 | 89.2 | 591 | 522 | 11.7 | 3.5 |
| Dextrose | 1:2 | 60 | 6.2 | 11,387 | 870 | 92.4 | 394 | 346 | 12.2 | 2.5 |

[a]Batch AN1005, 2.01% calcium d.b., P/α activity ratio = 28.9.
[b]Substrate at 30% d.s., adjusted to pH 5.5 before addition of enzyme.
[c]Determined at pH 6.3.

These starches generally have a protein content of about 0.30–0.35% or less. The use of protease-free α-amylase preparations will generally yield hydrolysates having less than about 0.10% protein. When using a prime starch, the prewash is not necessary but is preferred to obtain the best quality hydrolysate.

In order to provide a better understanding of the invention, the following exemplary and non-limiting examples are provided.

EXAMPLE I

Example I illustrates the effect of the concentration and type of the substrate material on the inactivation of the proteolytic enzyme activity during the heat treatment of an α-amylase enzyme preparation which is

EXAMPLE II

The procedure of Example I was repeated using TENASE as the α-amylase enzyme preparation. The heating was performed with and without the addition of a 42 D.E. corn syrup as a protective substrate material. The results are summarized in Table II.

TABLE II
EFFECT OF HEAT TREATMENT TIME ON INACTIVATION OF PROTEASE IN TENASE

| Heat Treatment | | Activity[a] U/g | | Inactivation, % | | P/α |
|---|---|---|---|---|---|---|
| Temp, °C. | Time, min | Protease[b] | α Amylase | Protease | α | Act. Ratio |
| Tenase (Batch LF-2155-C)[d] Diluted with 2 pbv Corn Syrup[c] | | | | | | |
| Untreated | | 3328 | 589 | — | — | 5.7 |
| 80 | 15 | 230 | 570 | 92.8 | 4.9 | 0.4 |
| 80 | 30 | Nil | 574 | 100 | 2.5 | <0.1 |
| Undiluted Tenase (Batch LF-2427-L)[e] | | | | | | |
| Untreated | | 9410 | 1724 | — | — | 5.5 |
| 80 | 15 | 6967 | N.D. | 26.0 | N.D. | N.D. |
| 80 | 30 | 3213 | 904 | 65.9 | 55.1 | 3.6 |
| 80 | 45 | 2051 | 662 | 78.2 | 69.4 | 3.3 |

[a]Activities of diluted LF-2155-C determined on vol. basis, calc. on wt. basis using a determined specific gravity 1.15.
[b]Protease act. det. at pH 6.5 for Batch LF-2155-C, 6.3 for Batch LF-2427-L.
[c]30% w/w 42 D.E. corn syrup containing 200 ppm d.b. added calcium.
[d]1.55% $Ca^{++}$, d.b.
[e]1.94% $Ca^{++}$, d.b.

EXAMPLE III

Samples of THERMAMYL (Batch AN 1050) α-amylase containing 0.50%, dry basis, calcium were heat treated for various periods of time at 80° C. The runs were performed both at the initial pH of the α-amylase preparation and at a pH adjusted to 5.5. Table III summarizes the results.

The results show that a 60 minute heat treatment at either pH produces protease/α-amylase activity ratios of less than 2. Extending the heating time to 120 minutes produced a ratio of 0.6, but at a sacrifice of 11%–13% of the α-amylase activity.

Slightly higher inactivation of both the protease and the α-amylase was obtained at a pH of 5.5 than at a pH of 6.4 due to generally reduced enzyme stability in the more acidic medium.

TABLE III
EFFECT OF HEAT TREATMENT TIME AND pH ON INACTIVATION OF PROTEASE IN THERMAMYL[a]

| Heat Treatment | | Activity, U/g | | Inactivation, % | | P/α |
|---|---|---|---|---|---|---|
| Temp, °C. | Time, min | Protease | α-Amylase | Protease | α-Amylase | Act. Ratio |
| pH 6.4 | | | | | | |
| Untreated | | 19,528 | 1,075 | — | — | 18.2 |
| 80 | 30 | 4,517 | 999 | 76.9 | 7.1 | 4.5 |
| 80 | 45 | 2,960 | 1,026 | 84.8 | 4.6 | 2.9 |
| 80 | 60 | 1,980 | 1,022 | 89.8 | 4.9 | 1.9 |
| 80 | 75 | 1,598 | 1,003 | 91.8 | 6.7 | 1.6 |
| 80 | 90 | 1,152 | 964 | 94.1 | 10.3 | 1.2 |
| 80 | 120 | 708 | 956 | 96.3 | 11.1 | 0.7 |
| pH 5.5 | | | | | | |
| Untreated | | 20,937 | 1,005 | — | — | 20.8 |
| 80 | 45 | 2,038 | 992 | 90.3 | 8.3 | 2.2 |
| 80 | 60 | 1,520 | 920 | 92.7 | 8.5 | 1.7 |
| 80 | 75 | 1,072 | 916 | 94.9 | 8.9 | 1.2 |
| 80 | 90 | 762 | 896 | 96.4 | 10.8 | 0.9 |
| 80 | 120 | 356 | 870 | 98.3 | 13.4 | 0.4 |

[a]Batch AN1050, 0.50% d.b. calcium, heat treated in the absence of carbohydrates.

EXAMPLE IV

Samples of various batches of THERMAMYL were heat treated at 80° C. for 60 minutes. Prior to the heat treatment, the calcium ion level of each batch was adjusted to a predetermined percentage by the addition of $CaCl_2$. Residual protease and α-amylase activities are shown in Table IV. As THERMAMYL calcium content is increased from 0.04% to 2.0%, protease inactivation decreases from 100% to 91%. In either case, α-amylase inactivation decreases from 25% at 0.04% calcium to about 5% at 1% calcium. Increasing calcium level to 2% results in increased inactivation of 7%–16%.

TABLE IV
EFFECT OF CALCIUM CONTENT ON INACTIVATION OF PROTEASE IN THERMAMYL[a]

| Batch | Total $Ca^{++}$ | | Protease Act., U/g | | α-Amylase Act., U/g | | Inactivation, % | | P/α |
|---|---|---|---|---|---|---|---|---|---|
| | % d.b. | % d.s. | Untreated | Ht. Trt. | Untreated | Ht. Trt. | Protease | α | Act. Ratio |
| AN1001 | 0.04 | 35.4 | 16,178 | 27 | 1069 | 802 | 99.8 | 25.0 | 0.03 |
| AN1001 | 0.25 | 34.3 | 15,218 | 64 | 1031 | 805 | 99.6 | 21.9 | 0.08 |
| AN1001 | 0.50 | 34.3 | 15,173 | 597 | 1010 | 904 | 96.1 | 10.5 | 0.66 |
| AN1050 | 0.50 | 26.0 | 19,528 | 1,980 | 1075 | 1022 | 89.8 | 4.9 | 1.94 |
| AN1001 | 1.00 | 34.6 | 15,659 | 853 | 971 | 935 | 94.6 | 3.7 | 0.91 |
| AN1069 | 1.00 | 29.0 | 19,746 | 2,229 | 1061 | 1000 | 88.7 | 5.7 | 2.23 |
| AN1001 | 2.00 | 33.9 | 15,899 | 869 | 984 | 911 | 94.5 | 7.4 | 0.95 |
| AN1005 | 2.01 | 30.4 | 29,211 | 2,645 | 999 | 834 | 90.9 | 16.5 | 3.17 |

[a]Heat treatment conducted in the absence of carbohydrate, 80° C., 60 minutes.

EXAMPLE V

Different batches of THERMAMYL containing 0.04% to 2.21% calcium were diluted with 2 parts of pH 5.5, 30% d.s., 42 D.E. corn syrup and heat treated at 80° C. for 30, 60 and 90 minutes and at 85° C. for 10, 20 and 30 minutes. In all cases, pH during heat treatment was 6.2–6.6. Data shown in Table V indicate that:

(a) Heat treating THERMAMYL, Batch AN1001, at 80° C. or 85° C. results in essentially complete protease inactivation with less than 7% loss in α-amylase activity (b) More α-amylase but less protease inactivation is obtained with Batch AN1002 than with the other batches of THERMAMYL. The reason for this is not understood.

(c) Data obtained with Batches AN1005 and 1009 indicate that (1) 90 minutes at 80° C. inactivates 93%–97% protease with 8% or less loss in α-amylase, and (2) 10–30 minutes at 85° C. inactivates 97%–100% protease along with about 7%–16% α-amylase.

TABLE V

PARAMETERS CONTROLLING SELECTIVE INACTIVATION OF PROTEASES IN THERMAMYL α-AMYLASE[a]

| Heat Treatment Temp, °C. | Time, min | After Heat Treatment Activity, U/ml Protease | α-Amylase | Inactivation, % Protease | α-Amylase | P/α Ratio |
|---|---|---|---|---|---|---|
| Batch AN1001 (0.04% d.b. Calcium) | | | | | | |
| 80 | 30 | 30 | N.D. | 99.6 | Nil[c] | 0.1 |
| 85 | 10 | 55 | 409 | 99.2 | 7.3 | 0.1 |
| 85 | 20 | 0 | 417 | 100 | 5.4 | 0.0 |
| 85 | 30 | 30 | 444 | 99.6 | Nil | 0.1 |
| Batch AN1002 (0.89% d.b. Calcium) | | | | | | |
| 80 | 30 | 2860 | N.D. | 69.8 | N.D. | 6.5[b] |
| 80 | 60 | 1965 | N.D. | 79.2 | N.D. | 4.5[b] |
| 80 | 90 | 1055 | 385 | 88.9 | 12.3 | 2.7 |
| 85 | 10 | 1385 | 361 | 85.3 | 17.8 | 3.8 |
| 85 | 20 | 405 | 341 | 95.7 | 22.3 | 1.2 |
| 85 | 30 | 270 | 356 | 97.8 | 18.9 | 0.8 |
| Batch AN1005 (2.01% d.b. Calcium) | | | | | | |
| 80 | 30 | 3291[c] | N.D. | 71.1 | Nil | 8.4 |
| 80 | 60 | 465[c] | 396 | 95.9 | Nil | 1.2 |
| 80 | 90 | 774[c] | N.D. | 93.2 | Nil | 2.0 |
| 85 | 10 | 400 | 363 | 96.5 | 7.9 | 1.1 |
| 85 | 20 | 0 | 342 | 100 | 13.2 | 0.0 |
| 85 | 30 | 40 | 359 | 99.6 | 8.9 | 0.1 |
| Batch AN1009 (2.21% d.b. Calcium) | | | | | | |
| 80 | 30 | 3680 | N.D. | 73.0 | N.D. | 9.1 |
| 80 | 60 | 1460 | N.D. | 89.3 | N.D. | 3.6 |
| 80 | 90 | 475 | 369 | 96.5 | 8.4 | 1.3 |
| 85 | 10 | 430 | 346 | 96.8 | 14.1 | 1.2 |
| 85 | 20 | 0 | 337 | 100 | 16.4 | 0.0 |
| 85 | 30 | 30 | 376 | 99.8 | 6.7 | 0.1 |

[a]Enzyme diluted with 2 pbv 30% 42 D.E. corn syrup prior to heat treatment.
[b]Assuming no loss in α-amylase activity of samples not assayed.
[c]Determined at pH 5.5.

EXAMPLE VI

The protease inactivation process was scaled-up for preparation of two large batches of enzyme for conversion studies. Batch sizes of 2600 and 6655 ml consisting of THERMAMYL (Batch AN1009) diluted with 2 pbv, 42 D.E. corn syrup at pH 5.5, 30% solids. The diluted enzyme (pH 6.2) was heated to 80° C. in 30 minutes in a steamheated water bath, held at temperature for 75 minutes and cooled to room temperature in about 30 minutes. Final pH was 5.9. Protease inactivation was 93%–96% with only about 3% loss in α-amylase activity. These two batches of heat-treated THERMAMYL were used to convert prime starch and mill starch, respectively, to dextrose hydrolyzates using the granular starch enzyme-heat-enzyme (EHE) process.

EXAMPLE VII

Corn grits were slurried in water and thinned with THERMAMYL enzyme preparations which had been heat treated to give various amounts of protease inactivation. One set was then saccharified at pH 5.5 with glucoamylase derived from *Aspergillus niger* and the other with β-amylase. The results are summarized in Tables VI and VII.

TABLE VI

EFFECT OF THERMAMYL PROTEASE/α-AMYLASE ACTIVITY RATIO ON PREPARATION OF DEXTROSE HYDROLYSATE FROM CORN GRITS[a]

| Run No. | 61 | 62 | 63 | 64 | 65 |
|---|---|---|---|---|---|
| THERMAMYL Treatment | | | | | |
| Batch | AN1001 | AN1005 | AN1009 | AN1009 | AN1001 |
| Temp, °C. | 80 | 80 | 80 | 80 | Untreated |
| Time, min | 30 | 60 | 60 | 30 | Untreated |
| P/α Act. Ratio | 0.1 | 1.2 | 3.6 | 9.1 | 15.5 |
| Hydrolyzate Analyses, d.b. | | | | | |
| % d.s. | 29.4 | 29.5 | 29.5 | 29.7 | 29.7 |
| Dextrose, % | 93.8 | 93.8 | 94.0 | 94.0 | 93.6 |
| Protein, % | 0.18 | 0.22 | 0.25 | 0.34 | 0.48 |
| Amino N., ppm | 31 | 36 | 42 | 57 | 89 |
| Filt. Rate, gal/hr/ft² | 12 | 16 | 14 | 14 | 16 |
| l/min/m² | 8 | 11 | 10 | 10 | 11 |
| Residue Analyses, Solubles Free Basis, d.b. | | | | | |
| % d.s. | 97.0 | 97.0 | 97.2 | 98.0 | 98.2 |
| Protein, % | 65.7 | 66.1 | 66.4 | 66.7 | 66.9 |
| Starch, % | 7.0 | 6.8 | 7.2 | 7.2 | 7.1 |
| Solubilization, % d.b. | | | | | |
| Starch | 99.1 | 99.2 | 99.1 | 99.1 | 99.1 |
| Total | 88.5 | 88.2 | 88.2 | 88.2 | 89.1 |

[a]Runs conducted by the 75° C. GS-EHE process, using 0.05% SO₂ prewash, 50 ppm calcium, pH 5.5 saccharification. Dosage of glucoamylase - 0.14 U/g.d.s.

TABLE VII

EFFECT OF THERMAMYL PROTEASE/α-AMYLASE ACTIVITY RATIO ON PREPARATION OF HIGH MALTOSE/MALTOTRIOSE SYRUP FROM CORN GRITS[a]

| Run No. | 54 | 55 | 56 | 57 | 58 |
|---|---|---|---|---|---|
| THERMAMYL Treatment | | | | | |
| Batch | AN1001 | AN1005 | AN1009 | AN1009 | AN1001 |

TABLE VII-continued
EFFECT OF THERMAMYL PROTEASE/α-AMYLASE ACTIVITY RATIO ON PREPARATION OF HIGH MALTOSE/MALTOTRIOSE SYRUP FROM CORN GRITS[a]

| Run No. | 54 | 55 | 56 | 57 | 58 |
|---|---|---|---|---|---|
| Temp, °C. | 80 | 80 | 80 | 80 | Untreated |
| Time, min | 30 | 60 | 30 | 30 | Untreated |
| P/α Act. Ratio | 0.1 | 1.2 | 3.6 | 9.1 | 15.5 |
| Hydrolyzate Analyses, d.b. | | | | | |
| % d.s. | 27.9 | 27.9 | 27.8 | 27.8 | 27.9 |
| D.E. | 47 | 46 | 46 | 46 | 46 |
| DP-1, % | 3 | 4 | 4 | 4 | 4 |
| -2, % | 53 | 52 | 51 | 53 | 53 |
| -3, % | 22 | 24 | 24 | 24 | 24 |
| Protein, % | 0.12 | 0.16 | 0.18 | 0.25 | 0.48 |
| Amino N., ppm | 20 | 26 | 32 | 47 | 83 |
| Filt. Rate, gal/hr/ft$^2$ | 14 | 14 | 16 | 16 | 16 |
| l/min/m$^2$ | 10 | 10 | 11 | 11 | 11 |
| Residue Analyses, Solubles Free Basis, d.b. | | | | | |
| % d.s. | 96.6 | 96.6 | 96.7 | 97.6 | 97.3 |
| Protein, % | 63.8 | 62.9 | 64.3 | 63.6 | 64.4 |
| Starch, % | 11.0 | 11.0 | 6.9? | 10.0 | 9.5 |
| Solubles, % | 1.3 | 2.4 | 1.2 | 0.8 | 1.2 |
| Solubilization, % d.b. | | | | | |
| Starch | 98.6 | 98.6 | 99.1 | 98.7 | 98.8 |
| Total | 88.4 | 88.6 | 88.5 | 88.6 | 88.9 |

[a]Runs conducted by the 75° C. GS-EHE process using 0.2% barley malt extract.

EXAMPLE VIII

The effect of protease level in high temperature liquefaction was studied briefly using THERMAMYL (Batch AN1009) which was either heat treated to inactivate proteases (P/α ratio=1.4) or used "as is" without protease inactivation (P/α ratio=32.9). Starch slurries at 25% w/w, pH 6.2, containing 200 ppm, d.b. added calcium were innoculated with 2 U/g d.s. THERMAMYL. Slurries were held at 50° C. for either 30 minutes or 24 hours prior to liquefaction. The long hold time was used to stimulate an extreme case in actual process conditions. Each slurry was thinned using indirect heating at 90° C. for 90 minutes, pH 6.2, and saccharified for 96 hours at pH 4.3, 60° C., with 14 glucoamylase U/100 g d.s. Average data obtained in this series and in a duplicate one are shown in Table VIII. Results indicate that increasing hold time from 30 minutes to 24 hours results in slightly more soluble protein in final hydrolyzates. However, the major factor influencing hydrolyzate protein content is the level of protease in the α-amylase. By using the treated THERMAMYL (low in protease), protein level is reduced from an average of 0.21% to 0.13%—a reduction of 38%.

TABLE VIII
EFFECT OF THERMAMYL PROTEASE CONTENT IN AN ENZYME-ENZYME DEXTROSE PROCESS

| Run No. | 1 & 5 | 2 & 6 | 3 & 7 | 4 & 8 |
|---|---|---|---|---|
| THERMAMYL | Untreated | Treated | Untreated | Treated |
| Protease/α Act. Ratio | 32.9 | 1.4 | 32.9 | 1.4 |
| Starch Slurry Holdtime, 50° C.[a] | 24 hr | 24 hr | 30 min | 30 min |
| Liquefaction[b] | | | | |
| % d.s. | 26.8 | 26.8 | 26.7 | 26.5 |
| D.E. | 22.2 | 21.9 | 19.2 | 19.1 |
| Saccharification[c] | | | | |
| % d.s. | 28.5 | 28.5 | 28.5 | 28.5 |
| Dextrose, % d.b. | 94.9 | 95.4 | 95.4 | 95.3 |
| Protein, % d.b. | 0.22 | 0.15 | 0.20 | 0.11 |
| Ins., % d.b. | 1.16 | 1.31 | 1.31 | 1.42 |

[a]A slurry of corn starch at 25% w/w containing 2 THERMAMYL U/g.d.s. + 200 ppm, d.b. added calcium was held at 50° C., pH 6.2 for indicated time prior to liquefaction.
[b]Indirect heating at 90° C., 90 min., pH 6.2.
[c]60° C., pH 4.3, 96 hr., 0.14 GA U/g.d.s.

EXAMPLE IX

The 75° C. GS-EHE process was used to evaluate corn grits and corn cleanings. The results are summarized in Tables IX and X. For comparative purposes, corn grits were converted by the 90° C. enzyme-enzyme process. The grits were prewashed with a 500 ppm SO$_2$ solution, liquefied by heating 90 minutes at 90° C., then converted with glucoamylase or malt extract. The results in Table XI show that hydrolyzate composition and quality are the same as obtained by the 75° C. process. However, starch solubilization and filtration rate are higher using the 75° C. process, making the 75° C. process a preferred method of conversion.

TABLE IX
CONVERSION OF CORN GRITS

| | GEH-32 |
|---|---|
| Prewash | 0.05% SO$_2$ |
| Solubles Removed, % d.b. | 1.8 |
| Saccharification | GA |
| Hydrolyzate Analyses, d.b. | |
| % d.s. | 29.4 |
| Dextrose, % | 94.5 |
| Protein, % | 0.33 |
| Amino N., ppm | 75 |
| Filtration Rate, gal/hr/ft$^2$ | 5 |
| Filtration Rate, liter/min/m$^2$ | 3 |
| Residue Analyses, d.b.[a] | |
| % d.s. | 97.5 |
| Starch, % | 13.8 |
| Protein, % | 67.3 |
| Solubles, % | 2.0 |

TABLE IX-continued

CONVERSION OF CORN GRITS

|  | GEH-32 |
|---|---|
| Solubilization, d.b. | |
| Total, %[b] | 88.1 |
| Starch, %[c] | 98.2 |

Conditions:
30% w/w SO$_2$ washed corn grits.
Thinned with 1 U P.I. THERMAMYL/g d.s.-50 ppm Ca$^{++}$-pH 6.5
Heated from 60° C. to 75° C. in 2 hr-heat treated at 100°C.
Converted with 0.14 U GA/g d.s.-pH 4.3-96 hr at 60° C.

[a]Corrected to solubles free basis.
[b]Includes solubles removed in prewash.
[c]Assumes no starch loss in prewash.

TABLE X

CONVERSION OF CORN CLEANINGS

|  | GEH-21 | GEH-25 |
|---|---|---|
| Prewash | 0.05% SO$_2$ | 0.05% SO$_2$ |
| Solubles Removed, % d.b. | 6.2 | 6.3 |
| Saccharification | Malt X | GA |
| Hydrolyzate Analyses, d.b. | | |
| % d.s. | 24.2 | 25.3 |
| Dextrose, % | — | 91.2 |
| D.E. | 44.1 | — |
| DP-1, % | 5.9 | — |
| DP-2, % | 54.5 | — |
| DP-3, % | 22.6 | — |
| DP-4+, % | 17.0 | — |
| Protein, % | 0.8 | 2.2 |
| Amino N., ppm | N.D. | 360 |
| Filtration Rate, gal/hr/ft$^2$ | <1 | <1 |
| Residue Analyses, d.b.[a] | | |
| % d.s. | 98.7 | 97.9 |
| Starch, % | 4.7 | 4.3 |
| Protein, % | 32.3 | 30.8 |
| Solubles, % | 1.1 | 1.2 |
| Solubilization, d.b. | | |
| Total, %[b] | 75.8 | 75.5 |
| Starch, %[c] | 98.4 | 98.5 |

Conditions:
30% w/w SO$_2$ washed corn cleanings; thinned with 1 U P.I. THERMAMYL/$^2$g d.s.-50 ppm Ca$^{++}$-pH 6.5-heated from 60° C. to 75° C. in 2 hr-heat treated at 100° C.-converted with 0.14 U GA/g d.s.-pH 4.3-96 hr at 60° C. (GEH-25) or 0.2% malt extract-pH 5.5-24 hr at 60° C. (GEH-24).

[a]Corrected to solubles free basis.
[b]Includes solubles removed in prewash.
[c]Assumes no starch loss in prewash.

TABLE XI

CONVERSION OF CORN GRITS USING THE 90° C. ENZYME-ENZYME PROCESS

| Run No. | GEH-59 | GEH-92 | GEH-60 | GEH-10 |
|---|---|---|---|---|
| Process | 90° C. E-E | GS-EHE | 90° C. E-E | GS-EHE |
| Saccharification | Malt X | Malt X | GA | GA |
| Hydrolyzate Analyses, d.b. | | | | |
| Dry Substance, % | 26.6 | 28.2 | 28.9 | 29.6 |
| Dextrose, % | N.D. | N.D. | 96.2 | 94.9 |
| D.E. | 41.0 | 44.6 | N.D. | N.D. |
| DP-1, % | 2.0 | 2.8 | N.D. | N.D. |
| DP-2, % | 53.2 | 51.6 | N.D. | N.D. |
| DP-3, % | 24.7 | 27.0 | N.D. | N.D. |
| DP-4+, % | 20.1 | 18.6 | N.D. | N.D. |
| Protein, % | 0.10 | 0.14 | 0.37 | 0.35 |
| Amino N., ppm | 20 | N.D. | 95 | 87 |
| Ca$^{++}$, ppm | 147 | N.D. | 102 | 47 |
| Filtration Rate, gal/hr/ft$^2$ | 1 | 13 | 4 | 14 |
| Filtration Rate, liter/min/m$^2$ | <1 | 9 | 3 | 10 |
| Residue Analyses, d.b.[a] | | | | |
| Dry Substance, % | 96.5 | 97.8 | 96.6 | 97.2 |
| Starch, % | 11.3 | 9.6 | 17.6 | 9.6 |
| Protein, % | 56.1 | 66.8 | 57.4 | 72.9 |
| Solubles, % | 1.7 | 1.5 | 3.2 | 1.6 |
| Solubilization, d.b. | | | | |
| Total, %[b] | 86.3 | 88.3 | 87.0 | 98.8 |
| Starch, %[c] | 98.3 | 98.7 | 97.5 | 98.8 |

Conditions:
30% w/w SO$_2$ washed corn grits-thinned with 1 U P.I. THERMAMYL/g d.s.-50 ppm Ca$^{++}$-pH 6.5-heated 2 hr at 90° C.-converted with 0.14 U GA/ g d.s.-96 hr at 60° C. or 0.2% malt extract-24 hr at 60° C.

[a]Corrected to solubles free basis.
[b]Does not include solubles lost in prewash (except GEH-92).
[c]Assume no starch lost in prewash.

EXAMPLE X

Heavy mill starch and a slurry of starch from which the protein was partially removed (second hydroclone underflow) were converted using the GS-EHE process to illustrate the use of wet milled high protein starch sources. The results are set forth in Table XII, XIII, and XIV.

TABLE XII

CONVERSION OF HEAVY MILL STARCH

| Run No. | GEH-78 | 80 | 82 | 79 | 81 | 83 |
|---|---|---|---|---|---|---|
| Saccharification pH | 4.3 | 4.3 | 4.3 | 5.5 | 5.5 | 5.5 |
| Make-up Dry Substance, % | 33.1 | 33.1 | 33.3 | 33.1 | 33.1 | 33.3 |
| Hydrolyzate Analyses, d.b. | | | | | | |
| Dry Substance, % | 33.5 | 33.0 | 33.5 | 33.2 | 33.0 | 33.7 |
| Dextrose, % | 94.4 | 94.3 | 94.7 | 93.5 | 93.5 | 93.6 |
| Protein, % | 0.48 | 0.48 | 0.49 | 0.40 | 0.40 | 0.41 |
| Amino N., ppm | 190 | 180 | 205 | 95 | 90 | 95 |
| Calcium, ppm | 48 | 55 | 38 | 64 | 60 | 60 |
| Filtration Rate, gal/hr/ft$^2$ | 7 | 6 | 10 | 2 | 7 | 7 |
| Filtration Rate, liter/min/m$^2$ | 5 | 4 | 7 | 1 | 5 | 5 |
| Residue Analyses, d.b.[a] | | | | | | |
| Dry Substance, % | 94.5 | 95.0 | 96.0 | 92.6 | 96.0 | 95.7 |
| Starch, % | 9.0 | 8.4 | 7.8 | 10.6 | 6.5 | 7.6 |
| Protein, % | 71.2 | 72.8 | 72.9 | 68.6 | 72.7 | 72.2 |
| Solubles, % | 0.8 | 1.2 | 1.5 | 2.5 | 0.9 | 0.8 |
| Solubilization, d.b. | | | | | | |
| Total, %[b] | 90.4 | 89.6 | 90.2 | 90.0 | 89.6 | 90.1 |
| Starch, %[c] | 99.0 | 99.0 | 99.1 | 98.8 | 99.2 | 99.1 |

Conditions:
30% w/w washed mill starch. Thinned with 1 U P.I. THERMAMYL/g d.s.-50 ppm Ca$^{++}$-pH 6.5 heated from 60° C. to 75° C. in 2 hr-heat treated at 100° C. Converted with 0.14 U GA/g d.s.-pH 4.3-96 hr at 60° C. or 0.18 U GA/g d.s.-pH 5.5-96 hr at 60° C.

[a]Corrected to solubles free basis.
[b]Does not include solubles removed in prewash.
[c]Assumes no starch lost in prewash.

TABLE XIII

DEXTROSE HYDROLYZATES PREPARED FROM SECOND HYDROCLONE UNDERFLOW

| Run No. | DU-1 | DU-2 | DU-3 | DU-4 | DU-5 |
|---|---|---|---|---|---|
| $H_2O$ Prewash | 1X | 1X | 1X | 3X | 3X |
| Thinning | | | | | |
| Enzyme | | | P.I. THERMAMYL | | |
| Dosage, U/g d.s. | 1 | 1 | 1 | 1 | 1 |
| pH | 5.5 | 6.5 | 5.5 | 6.5 | 5.5 |
| Added $Ca^{++}$, ppm d.b. | 50 | 50 | 50 | 50 | 50 |
| Saccharification | | | | | |
| GA, U/g d.s. | 0.14 | 0.14 | 0.14 | 0.14 | 0.18 |
| pH | 4.3 | 4.3 | 4.3 | 4.3 | 5.5 |
| Hydrolyzate Analyses, d.b. | | | | | |
| Dry Substance, % | 33.7 | 33.7 | 32.9 | 32.9 | 32.7 |
| Dextrose, % | 94.8 | 94.4 | 94.6 | 65.1 | 95.0 |
| Protein, % | 0.19 | 0.24 | 0.16 | 0.22 | 0.13 |
| Amino N., ppm | 60 | 85 | 55 | 75 | 20 |
| $Ca^{++}$, ppm d.b. | 60 | 58 | 58 | 62 | 68 |
| Filtration Rate, gal/hr/ft² | 8 | 5 | 13 | 8 | 9 |
| Filtration Rate, liter/min/m² | 5 | 3 | 9 | 5 | 6 |
| Total Insolubles, % d.b. | 2.8 | 3.1 | 2.8 | 3.0 | 2.7 |

Conditions:
30% washed second hydroclone underflow.
Dosed and heated from 60° C. to 75° C. in 2 hr
heat treated at 100° C.
Converted with GA-96 hr at 60° C.

TABLE XIV

MALT CONVERSION OF SECOND HYDROCLONE UNDERFLOW

| Run No. | LK-106 | LK-107 | LK-108 | GEH-22 |
|---|---|---|---|---|
| Prewash | None | 6X-$H_2O$ | 12X-$H_2$ | 0.05% $SO_2$ |
| Solubles Removed, % d.b. | None | 0.7 | 0.7 | 0.9 |
| Hydrolyzate Analyses, d.b. | | | | |
| Dry Substance, % | 31.0 | 31.0 | 31.0 | 30.9 |
| D.E., % | 43.4 | 43.6 | 42.1 | 43.1 |
| DP-1, % | 0.9 | 0.9 | 0.8 | 1.3 |
| DP-2, % | 57.0 | 56.6 | 58.0 | 54.7 |
| DP-3, % | 20.8 | 18.6 | 18.5 | 22.8 |
| DP-4+, % | 21.3 | 23.9 | 22.7 | 21.2 |
| Protein, % | 0.47 | 0.10 | 0.09 | 0.16 |
| Solubilization, d.b. | | | | |
| Total, % | 96.9 | 96.8 | 96.7 | 96.8 |

Conditions:
30% w/w washed second hydroclone underflow. Thinned with 1 P.I. THERMAMYL U/g.d.s., pH 6.5, 50 ppm added calcium, temperature raised from 60° C. to 75° C. in 2 hours, heat treated at 100° C. Converted with 0.2% barley malt extract, pH 5.5, 60° C., 24 hours.

TABLE XV

CONVERSION OF LIGHT MILL STARCH: EFFECT OF SACCHARIFICATION TIME

| Saccharification Time | Dextrose, % d.s. | | Dextrose, % d.b. | | Protein, % d.b. | | Amino Nit, ppm d.b. | |
|---|---|---|---|---|---|---|---|---|
| pH | 4.3 | 5.5 | 4.3 | 5.5 | 4.3 | 5.5 | 4.3 | 5.5 |
| 24 hr | 30.6 | 30.7 | 90.2 | 86.1 | 0.41 | 0.35 | 130 | 80 |
| 48 hr | 31.3 | 30.8 | 93.9 | 91.9 | 0.46 | 0.38 | 160 | 80 |
| 72 hr | 30.9 | 30.8 | 94.7 | 93.6 | 0.47 | 0.40 | 170 | 85 |
| 96 hr | 31.2 | 30.9 | 94.5 | 93.4 | 0.49 | 0.41 | 180 | 85 |
| 115 hr | 31.2 | 30.9 | 94.5 | 94.2 | 0.50 | 0.42 | 190 | 100 |

Condition:
30% w/w washed milled starch (3X-$H_2O$)-thinned with
1 U P.I. THERMAMYL/g d.s.-50 ppm²$Ca^{++}$-pH 6.5
heated from 60° C. to 75° C. in 2 hr-heat treated at 100° C.
Converted with 0.14 GA/g d.s.-pH 4.3-96 hr at 60° C.
or 0.18 U GA/g d.s.-pH 5.5-96 hr at 60° C.
Run No. GEH-74 for 4.3 pH; GEH-75 for 5.5 pH.

TABLE XVI

CONVERSION OF LIGHT MILL STARCH: EFFECT OF SACCHARIFICATION pH

| Run No. | GEH-66 | GEH-70 | GEH-67 | GEH-69 |
|---|---|---|---|---|
| Prewash | 3X-$H_2O$ | 3X-$H_2O$ | 3X-$H_2O$ | 3X-$H_2O$ |
| Solubles Removed | 8.8 | 9.3 | 8.7 | 9.3 |
| Make-up Dry Substance | 32.7 | 30.5 | 33.1 | 30.5 |
| Saccharification pH | 5.5 | 5.5 | 4.3 | 4.3 |
| Hydrolyzate Analyses, d.b. | | | | |
| Dry Substance, % | 33.8 | 31.0 | 34.0 | 30.9 |
| Dextrose, % | 94.2 | 93.5 | 95.3 | 94.7 |
| Protein, % | 0.29 | 0.47 | 0.38 | 0.53 |
| Amino N., ppm | 60 | 110 | 160 | 215 |
| Filtration Rate, gal/hr/ft² | 4 | 4 | 9 | 10 |
| Filtration Rate, liter/min/m² | 3 | 3 | 6 | 7 |
| Residue Analyses, d.b.[a] | | | | |
| Dry Substance, % | 96.9 | 95.8 | 97.8 | 96.5 |
| Starch, % | 10.6 | 4.7 | 11.6 | 4.0 |
| Protein, % | 70.0 | 75.9 | 67.9 | 76.4 |
| Solubles, % | 2.3 | 6.0 | 2.0 | 5.4 |
| Solubilization, d.b. | | | | |
| Total, %[b] | 90.9 | 91.9 | 91.3 | 92.0 |
| Starch, %[c] | 98.9 | 99.6 | 98.8 | 99.6 |

Conditions:
30% w/w washed mill starch-thinned with 1 U P.I.
THERMAMYL/ g d.s.-50 ppm $Ca^{++}$-pH 6.5-heated
-pH6.5-(heated from
60° C. to 75° C. in 2 hr-heat treated at 100° C.-converted
with 0.14 U GA/ g d.s.-pH 4.3-96 hr at 60° C. or 0.18
U GA/g d.s.-pH 5.5-96 hr at 60° C.

[a] Corrected to solubles free basis.
[b] Does not include solubles removed in prewash.
[c] Assumes no starch removed in prewash.

EXAMPLE XI

Light mill starch was converted using the 75° C. GS-EHE process by varying various process parameters.

Table XV illustrates the effect of saccharification time on the hydrolysate composition. Table XVI illustrates the effect of saccharification pH. Table XVII, Run GEH-71 illustrates the effect of adding additional α-amylase to the saccharification step. Run GEH-72 uses MAXAMYL instead of THERMAMYL as the α-amylase. Run GEH-73 represents the heating of the thinned starch to 121° C. rather than the standard 100° C. The light mill starch was also converted with a combination of Thermamyl and glucoamylase at a temperature of 60° C. The results are in Table XVIII.

TABLE XVII

CONVERSION OF LIGHT MILL STARCH: EFFECT OF α-AMYLASE AND HEAT TREATMENT TEMPERATURE

| Run No. | GEH-71[a] | GEH-72[b] | GEH-73[c] |
|---|---|---|---|
| Saccharification pH | 5.5 | 4.3 | 4.3 |
| Hydrolyzate Analyses, d.b. | | | |
| Dry Substance, % | 31.0 | 30.6 | 31.4 |
| Dextrose, % | 93.5 | 94.9 | 90.7 |
| Protein, % | 0.56 | 0.49 | 0.62 |
| Amino N., ppm | 135 | 200 | 450 |
| $Ca^{++}$, ppm | 69 | 217 | 109 |
| Filtration Rate, gal/hr/ft² | 6 | <1 | 4 |
| Filtration Rate, liter/min/m² | 4 | <1 | 3 |
| Residue | | | |

TABLE XVII-continued
CONVERSION OF LIGHT MILL STARCH: EFFECT OF α-AMYLASE AND HEAT TREATMENT TEMPERATURE

| Run No. | GEH-71[a] | GEH-72[b] | GEH-73[c] |
|---|---|---|---|
| Analyses, d.b.[d] | | | |
| Dry Substance, % | 95.8 | Discarded | 95.5 |
| Starch, % | 3.9 | " | 12.1 |
| Protein, % | 76.9 | " | 71.7 |
| Solubles, % | 6.1 | " | 6.6 |
| Solubilization, d.b | | | |
| Total, %[e] | 91.9 | " | 91.5 |
| Starch, %[f] | 99.6 | " | 98.9 |

[a]0.5 U P.I. THERMAMYL/g d.s. added during saccharification.
[b]Thinned with 3 U MAXAMYL/g d.s.-200 ppm d.b. Ca++.
[c]Heat treated 15 min at 121° C.
[d]Corrected to solubles free basis.
[e]Does not include solubles removed in prewash.
[f]Assumes no starch lost in prewash

TABLE XVIII
CONVERSION OF LIGHT MILL STARCH USING 60° C. PROCESS

| Run No. | GEH-76 | GEH-77 |
|---|---|---|
| Make-up Dry Substance, % | 15.2 | 15.2 |
| Digestion Conditions | 96 hr at pH 5.5 | 24 hr at pH 5.5 |
|  |  | 24 hr at pH 4.3 |
| Hydrolyzate Analyses, d.b. | | |
| Dry Substance | 9.3 | 10.0 |
| Dextrose, % | 93.7 | 94.4 |
| Protein | 1.5 | 1.3 |
| Amino N., ppm | 600 | 450 |
| Ca++, ppm | 33 | 33 |
| Filtration Rate, gal/hr/ft$^2$ | 18 | 21 |
| Filtration Rate, liter/min/m$^2$ | 12 | 14 |
| Residue Analyses, d.b.[a] | | |
| Dry substance, % | 94.2 | 93.4 |
| Starch, % | 81.7 | 81.7 |
| Protein, % | 14.4 | 15.4 |
| Solubles, % | Nil | 0.2 |
| Solubilization, d.b. | | |
| Total[b] | 52.7 | 56.1 |
| Starch, %[c] | 58.7 | 61.7 |
| Conditions: | | |
| 15% washed mill starch. | | |
| Converted with 2 U P.I. THERMAMYL/g d.s.-0.25 U GA/g d.s. | | |

[a]Corrected to solubles free basis.
[b]Does not include solubles removed in prewash.
[c]Assumes no starch lost in prewash.

EXAMPLE XII

Corn grits were converted using the 75° C. GS-EHE process. One batch was prewashed using lake water and the second using 0.1% SO$_2$ solution. The results are set forth in Table XIX.

TABLE XIX
COMPARISON OF H$_2$O AND SO$_2$ PREWASHING OF CORN GRITS

| | Type of Wash | |
|---|---|---|
| | H$_2$O | 0.1% SO$_2$ |
| Prewashing | | |
| Grit Solubles, % d.b. | 2.2 | 3.4 |
| Hydrolyzate Analyses | | |
| % d.s. | 29.44 | 29.50 |
| Dextrose, % d.b. | 92.2 | 95.4 |
| Protein, % d.b. | 0.25 | 0.35 |
| Amino N, ppm d.b. | 53 | 112 |
| Ca++, ppm d.b. | 225 | 173 |
| Filtration Rate (gal/hr/ft$^2$) | 6.1 | 14.9 |
| Residue Analyses[a] | | |
| % d.s. | 95.8 | 95.5 |
| Protein, % d.b. | 63.3 | 62.9 |
| Starch, % d.b. | 13.1 | 11.0 |
| Solubles, % d.b. | 2.1 | 1.7 |
| Unconverted Starch, % d.b.[b] | 1.8 | 1.4 |

Conditions:[c]
30% grits (#1 Grit, 6/3/74)
Thinned with 1 unit P.I. THERMAMYL/g d.s.-pH 6.5-200 ppm Ca++
Programmed heat-up from 60° C. to 75° C.
Heat treated at 100° C.
Converted with 0.14 unit GA/g d.s.-pH 4.3-96 hr at 60° C.

[a]Values corrected to solubles free basis.
[b]Based on starch recovered in EPC; assumes no loss in washing.
[c]Dosages based on starch dry substance.

EXAMPLE XIII

Prime starch was converted to a soluble starch hydrolysate by the following procedure.

A 30% w/w aqueous slurry was prepared, the pH adjusted to 6.2; 300 ppm calcium ion added and the slurry inoculated with 1.2 U α-amylase/g.d.s. (MAXAMYL; P/α=0.9). The slurry was heated to 88° C. and held for two hours. It was then heated to 127° C. and held for 15 minutes. The slurry was then cooled to 85° C.; inoculated with 0.6 U α-amylase/g.d.s. and held for 3 hours.

This was then cooled to 60° C., sufficient lake water added to reduce the solids content to 25%, w/w, the pH adjusted to 4.3 and the slurry inoculated with 0.18 U glucoamylase/g.d.s. These conditions were then maintained for 96 hours. The hydrolysate contained 95.9% dextrose, d.b., a protein content of 0.08% d.b. and 1.4% total insolubles, d.b.

While the invention has been described in connection with specific embodiments thereof, it will be understood that it is capable of further modification, and this application is intended to cover any variations, uses or adaptions of the invention following, in general, the principles of the invention and including such departures from the present disclosure as come within the known or customary practice in the art to which the invention pertains and as may be applied to the essential features hereinbefore set forth, and as fall within the scope of the invention.

What is claimed is:

1. A process for the selective inactivation of proteolytic enzyme impurities in a bacterial α-amylase enzyme preparation derived from *Bacillus licheniformis* comprising the steps of:
   (a) introducing into the preparation sufficient water soluble calcium salt to yield a total calcium ion concentration of from about 0.5% to about 1.5%, dry basis;
   (b) heating the resulting mixture to a temperature in the range of from about 70° C. to about 90° C.; and
   (c) maintaining the temperature for a period of time sufficient to substantially completely inactivate the proteolytic enzyme without substantially reducing the α-amylase activity.

2. A process in accordance with claim 1, wherein the pH of the preparation is in the range of from about 5 to about 8.

3. A process in accordance with claim 1, wherein the temperature is maintained for a period of from about 30 minutes to about 3 hours.

4. A process in accordance with claim 1, wherein at least a portion of said calcium ion was originally present in said enzyme preparation.

* * * * *